United States Patent [19]

Sawyer et al.

[11] Patent Number: 4,847,249

[45] Date of Patent: Jul. 11, 1989

[54] TRIAZINE SALT

[76] Inventors: David A. Sawyer, The Wellcome Research Laboratories, Langley Court; Frederick C. Copp, 32, Stanley Avenue, both of Beckenham, Kent, England

[21] Appl. No.: 56,136

[22] Filed: May 29, 1987

[30] Foreign Application Priority Data

May 30, 1986 [GB] United Kingdom ............... 8613183

[51] Int. Cl.$^4$ ................... C07D 253/06; A61K 31/53
[52] U.S. Cl. ..................................... 514/242; 544/182
[58] Field of Search .......................... 544/182; 514/242

[56] References Cited

U.S. PATENT DOCUMENTS 4,486,354 12/1984 Baxter et al. ..................... 260/465 E
4,602,017 7/1986 Sawyer et al. ...................... 544/182

FOREIGN PATENT DOCUMENTS 21121   1/1981  European Pat. Off. .
24351   3/1981  European Pat. Off. .
93186  11/1983  European Pat. Off. .
142306  5/1985  European Pat. Off. .

OTHER PUBLICATIONS

Yalcindag, *Chemical Abstracts*, vol. 94, entry 162824q (1981).

*Primary Examiner*—John M. Ford
*Attorney, Agent, or Firm*—Donald Brown

[57] ABSTRACT 3,5-Diamino-6-(2,3-dichlorophenyl)-1,2,4-triazine isethionate is provided. This salt has high water solubility and thus advantageously allows parenteral administration in the form of a sterile aqueous solution suitable for injection.

3 Claims, No Drawings

TRIAZINE SALT

This invention relates to a highly soluble triazine salt.

It is known that certain 3,5-Diamino-6-(substituted phenyl)-1,2,4-triazines are active in the treatment of CNS disorders, such as psychiatric and neurological disorders, and are also useful as anticonvulsants, for example in the treatment of epilepsy. These triazines are also non-depressant at therapeutic dose levels and are therefore advantageous as compared with depressant anti-epileptics such as phenobarbitone.

A particularly preferred compound of this type is 3,5-Diamino-6-(2,3-dichlorophenyl)-1,2,4-triazine (e.g. European Pat. No. 21121). For parenteral administration the compound is desirably presented in the form of a sterile aqueous solution suitable for injection. However, the compound is only sparingly soluble in water necessitating administration of an undesirably large volume of solution to achieve a therapeutic dosage. Common pharmaceutically acceptable salts of the compound e.g. the citrate, tartrate, maleate, sterate, succinate, fumarate, phosphate, sulphate, benzenesulphonate, 4-toluenesulphonate, 4-acetoamidobenzoate and N-acetylglycinate, all have sloubilities below 20mg/ml. However, we have surprisingly found that the 2-hydroxyethanesulphonate, hereinafter referred to as the isethionate, has a much higher water solubility.

Thus the present invention provides 3,5-Diamino-6-(2,3-dichlorophenyl)-1,2,4-triazine isethionate.

The present invention provides in particular crystalline 3,5-Diamino-6-(2,3-dichloropheynl)-1,2,4-triazine isethionate.

The isethionate salt of this compound may be prepared by reacting the compound or its salt with isethionic acid and its salt.

Thus the present invention also provides a process for producing 3,5-Diamino-6-(2,3-dichlorophenyl)-1,2,4-triazine isethionate which process comprises reacting 3,5-Diamino-6-(2,3-dichlorophenyl)-1,2,4-triazine with isethionic acid.

Preferably the molar ratio of triazine to acid is from 1:3 to 3:1, and in particular approximately 1:1.

Isethionic acid decomposes and is therefore conveniently made in situ when carrying out the process of the invention. For example an alkali metal isethionate in solution is converted to isethionic acid e.g. by passing an aqueous solution of the isethionate through an $H^+$ ion-exchange resin, and the triazine is then mixed with the resulting acid solution. Typically the reaction solvent is water and when this is so the reaction may be performed at temperatures of from 4° to 50° C., conveniently at ambient temperature and without the need for any pH adjusters or other additives.

The isethionate salt formed may be recrystallized from e.g. Industrial Methylated Spirit to produce crystals of 3,5-Diamino-6-(2,3-dichlorophenyl)-1,2,4-triazine isethionate which readily dissolve in water.

The present invention further provides a process for producing 3,5-Diamino-6-(2,3-dichlorophenyl)-1,2,4 triazine isethionate which process comprises reacting a 3,5 Diamino-6-(2,3-dichlorophenyl)-1,2,4 triazine salt other than isethionate with an isethionate anion. Preferably the ratio of salt to anion is from 1:50 to 50:1. More preferably the ratio is approximately 1:10. Preferably the reaction is carried out by eluting a solution of the salt in methanol through a column of isethionate anion exchange resin.

In this case the 3,5-Diamino-6-(2,3 dichlorophenyl)-1,2,4 triazine salt is preferably 3,5 Diamino-6-(2,3 dichlorophenyl)-1,2,4 triazine mesylate.

3,5-Diamino-6-(2,3-dichlorophenyl)-1,2,4-triazine may be made as the base by the process described in European Pat. No. 21121 by cyclization 2-(2,3-dichlorophenyl)-2-(guanidinoimino) acetonitrile.

An alternative method of making the triazine base is to react aminoguanidine with benzoyl cyanide. This may be done by reacting acidified (e.g. with an inorganic acid) aminoguanidine bicarbonate with benzoyl cyanide and refluxing in a $C_1$–$C_4$ alkanol.

The cyclization reaction is normally carried out by refluxing in an alkanol, preferably a $C_{1-4}$ alkanol such as methanol or ethanol, in the presence of a strong base such as potassium hydroxide. The preparation of the starting compound for the cyclization reaction is analogous to that described in the literature i.e. U.S. Pat. No. 3,637,688 for structurally related compounds.

We have now found that the cyclisation reaction can be carried out in the presence of a strong acid.

The present invention also provides a pharmaceutical formulation comprising 3,5-Diamino-6-(2,3-dichlorophenyl)-1,2,4-triazine isethionate, and a pharmaceutically acceptable diluent or carrier.

Although the isethionate salt is advantageoulsy administered as a sterile aqueous formulation, either orally or parenterally, it may also be prepared as a suppository, or applied topically as an ointment, cream or powder.

For oral administration the salt may be presented in a draught, in water or in a syrup, in capsules or sachets in the dry state or in non-aqueous suspension in which suspending agents may be included. Alternatively, the salt may be presented as an effective unit dosage, for instance, compressed as a table or the like. The usual pharmaceutically acceptable additives may also be present e.g. flavouring, colouring, preserving, suspending, thickening or emulsifying agents.

The present invention also provides sterile aqueous pharmaceutical formulations comprising 3,5-Diamino-6-(2,3-dichlorophenyl)-1,2,4-triazine isethionate.

The salt will be present in the aqueous formulation of the present invention in an amount sufficient to be effective against CNS disorders in vivo and the formulation may be in unit dosage form. Up to about 250mg/ml of the salt, calculated as free base, may be present in aqueous formulation. However, typical concentrations of the salt in solution are 10 to 70mg/ml, preferably 10 to 50mg/ml. For parenteral administration the salt may be presented in sterile aqueous injection solutions which may contain therapeutically acceptable accessory ingredients such as anti-oxidant, buffers and agents to adjust the osmolarity of the solution. Preferably anions such as chloride and phosphates are not present in the solution, since these tend to exchange with the isethionate salt to form precipitates.

The present invention also provides a process for producing an aqueous formulation comprising 3,5-Diamino-6-(2,3-dichlorophenyl)-1,2,4-triazine isethionate which process comprises dissolving the isethionate in aqueous media, suitably sterile water for injection. The solution may be diluted before use to the required concentration. It is not generally necessary to adjust the pH of the solution.

The present invention also relates to a method for treating a human or animal suffering from or susceptable to a CNS disorder by administering to the human or animal an effective dose of 3,5-Diamino-6-(2,3-dichlorophenyl)-1,2,4-triazine isethionate.

The present invention also relates to a method for treating a human or animal suffering or susceptible to a CNS disorder by administering to the human or animal an effective amount of a pharmaceutical formulation comprising 3,5-Diamino-6-(2,3-dichlorophenyl)-1,2,4-triazine isethionate and a pharmaceutically acceptable diluent or carrier.

The present invention further relates to a method for treating a human or animal suffering from or susceptible to a CNS disorder by administering to the human or animal an effective amount of a sterile aqueous formulation comprising 3,5-Diamino-6-(2,3-dichlorophenyl)-1,2,4-triazine isethionate. Preferably treatment is by parenteral administration.

If the aqueous formulation is to be adminstered parenterally then, preferably, it is a simple aqueous solution which is diluted with, and infused in, a dextrose solution e.g. a 5% dextrose solution, at the time of administration. If dextrose is present in the aqueous formulation for long periods of time at elevated temperature e.g. during long-term storage, there is a tendency for the monoglucoside of the isethionate salt to form, and it is therefore preferred to add the dextrose at the time of administration.

The present invention also provides 3,5-Diamino-6-(2,3-dichlorophenyl)-1,2,4-triazine isethionate for use in a method of treatment of the human or animal body by surgery or therapy or of diagnosis practised on the human or animal body.

The present invention also provides a pharmaceutical formulation comprising 3,5-Diamino-6-(2,3-dichlorophenyl)-1,2,4-triazine isethionate and a pharmaceutically acceptable diluent or carrier for use in a method of treatment of the human or animal body by surgery or therapy or of diagnosis practised on the human or animal body.

The present invention further provides an aqueous formulation comprising 3,5-Diamino-6-(2,3-dichlorophenyl)-1,2,4-triazine isethionate for use in a method of treatment of the human or animal body by surgery or therapy or of diagnosis practised on the human or animal body.

The salt, and pharmaceutical and aqueous formulations of the present invention may be used for the treatment of CNS disorders, and in particular epilepsy, in humans.

The dose is normally from 0.1mg/kg to 30mg/kg per day of the salt, calculated as free base, preferably 0.3mg/kg to 6mg/kg per day. The dosage for adult humans is generally from 8mg to 2400mg per day of the salt, calculated as the free base, and preferably 25 to 400mg per day and this may be given as a single dose or in divided doses. Since the salt is extremely long acting, it may often be advantageous to administer an initial dose of 70 to 2400mg the first day and the a lower dose of 20 to 1200mg on subsequent days.

The following Examples illustrate the preparation of the salt of the invention and formulations containing it.

EXAMPLE 1

Preparation of
3,5-Diamino-6-(2,3-dichlorophenyl)-1,2,4-triazine

A solution of 2,3-dichlorophenyl cyanide (32g, 0.26M) in dimethylsulphoxide (80mls) was added dropwise to a stirred suspension of aminoguanidine bicarbonate (81.67g, 0.6M) which had been treated with 8N aqueous nitric acid (400mls) at a temperature of about 25° C. The mixture was stirred for three hours, then left to stand at room temperature for seven days. The cooled mixture was stirred and basified with 0.880 aqueous ammonia (400mls) at 20° C., then stirred with ice cooling for thirty minutes, filtered and the resulting solid washed thoroughly with water and finally dried in vacuo. The above solid was added to a 10% solution of potassium hydroxide pellets in methanol (400mls) and the solution heated to reflux for one and a half hours. When cool the solution was evaporated down in vacuo, treated with ice water (800mls) then stirred for thirty minutes and filtered. The residue was dried and recrystallised from isopropanol to give 3,5-Diamino-6-(2,3-dichlorophenyl)-1,2,3-triazine. Yield 6.8g (15.6%), m.p. 216°–218° C.

EXAMPLE 2

Preparation of
3,5-Diamino-6-(2,-dichlorophenyl)-1,2,4-triazine

Aminoguanidine bicarbonate (48.1g, 0.354M), followed by a solution of 2,3-dichlorophenyl cyanide (40.0g, 0.2M) in acetonitrile (160mls), was added to a stirred solution of concentrate sulphuric acid (441g) in water (240mls). The mixture was stirred at 20°–30° C. for forty-eight hours and then filtered. The solid was added to a cooled solution of sodium hydroxide (28g) in water (150mls) below 30° C. The suspension was filtered and the resulting solid washed thoroughly with water and dried at 80° C. The above solid was added to propan-1-ol (308mls) and the solution heated to reflux for one and half hours. When cool the solid was filtered, dried at 100° C. and then recrystallised from propan-1-ol to give 3,5-Diamino-6-(2,3-dichlorophenyl)-1,2,4-triazone. Yield 21.0g (41%), m.p. 216°–218° C.

EXAMPLE 3

Preparation of
3,5-Diamino-6-(2,3-dichlorophenyl)-1,2,4-triazine isethionate

A solution of sodium isethionate (148g, 1.0M) in water (4.9 liters) was passed down a column of IR 120 (H) ion-exchange resin and eluted with water. 3,5-Diamino-6-(2,3-dichlorophenyl)-1,2,4-triazine (256g, 1.0M) was dissolved in the resulting isethionic acid, and the solution filtered and evaporated in vacuo. The residue was recrystallised from Industrial Methylated Spirit to afford 3,5-Diamino-6-(2,3-dichlorophenyl)-1,2,4-triazine isethionate. Yield 273.3g (72%), m.p. 242° C.

EXAMPLE 4

Preparation of 3,5
Diamino-6-(2,3,dichlorophenyl)-1,2,4-triazine isethionate

50mM of Amberlite (trade mark) IR-45 (OH) was mixed with 15 mM (10ml) aqueous isethionic acid and the resulting material was packed into a column. The column was then washed with methanol. 0.7g (2mM) of a methanolic solution of 3,5 Diamino-6-(2,3 dichlorophenyl)-1,2,4 triazine mesylate was eluted through the column. The elutant was recrystalised from Industrial Methylated Spirits and gave 3,5 Diamino-6-(2,3-dichlorophenyl)-1,2,4 triazine isethionate: yield 300mg (40%), m.p. 242°–243° C.

EXAMPLE 5

74.625g (0.195M) of 3,5-Diamino-6-(2,3-dichlorophenyl)-1,2,4-triazine isethionate was added to and dissolved in around 900ml of water for injections BP, and diluted to 1000ml with further water for injections BP, to give an aqeuous solution containing isethionate salt equivalent to 50mg/ml of the 3,5-Diamino-6-(2,3-dichlorophenyl)-1,2,4-triazine base. This solution was acceptable on tonicity grounds.

EXAMPLE 6

14.925g (0.039M) of 3,5-Diamino-6-(2,3-dichlorophenyl)-1,2,4-triazine isethionate as added to a solution of 43.8g (0.221M) of Dextrose Monohydrate in around 900ml of water for injections BP and diluted to 1000ml with further water for injections BP, to give an aqueous solution containing isethionate salt equivalent to 10mg/ml of the 3,5-Diamino-6-(2,3-dichlorophenyl)-1,2,4-triazine base. This solution was acceptable on tonicity grounds.

What we claim is:
1. 3,5-diamino-6-(2,3-dichlorophenyl)-1,2,4-triazine isethionate.
2. A sterile aqueous injectable formulation comprising 3,5-Diamino-6-(2,3-dichlorophenyl)-1,2,4-triazine isethionate and water.
3. A formulation comprising 3,5-Diamino-6-(2,3-dichlorophenyl)-1,2,4-triazine isethionate and a pharmaceutically acceptable carrier therefore.

* * * * *